United States Patent
Doehling et al.

[11] Patent Number: 5,865,855
[45] Date of Patent: Feb. 2, 1999

[54] BIS-PYRAZOLE AZA COMPOUNDS, PROCESSES FOR MAKING THEM, AND HAIR DYE COMPOSITIONS CONTAINING THESE COMPOUNDS

[75] Inventors: Annelie Doehling, Muenster; Wolfram Geibel, Huenfeld, both of Germany; Otto Goettel, Marly, Switzerland

[73] Assignee: Wella Aktiengesellschaft, Darmstadt, Germany

[21] Appl. No.: 103,995

[22] Filed: Jun. 24, 1998

[30] Foreign Application Priority Data

Jul. 16, 1997 [DE] Germany .................. 197 30 412.5

[51] Int. Cl.⁶ .................. A61K 7/13; C07D 403/12
[52] U.S. Cl. .................. 8/409; 8/405; 8/407; 8/639; 8/643; 548/365.1
[58] Field of Search .............. 548/365.1; 8/405, 8/407, 409

[56] References Cited

FOREIGN PATENT DOCUMENTS

| 0 375 977 | 7/1990 | European Pat. Off. |
| 0 740 931 A1 | 11/1996 | European Pat. Off. |

OTHER PUBLICATIONS

Lieblings Annalen Der Chemie 717, pp. 118–123 By H. Dorn and H. Dilcher, 1968.
Synthesis 1984, 148–149 By P. G. Baraldi et al.

*Primary Examiner*—Laura L. Stockton
*Attorney, Agent, or Firm*—Michael J. Striker

[57] ABSTRACT

The new bis-pyrazole aza compounds have the formula (I):

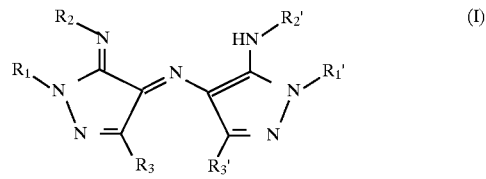

wherein $R_1$, $R_1'$, $R_2$, $R_2'$, $R_3$ and $R_3'$ are the same or different, and are each, independently of each other, H, a straight, branched or cyclic alkyl group having 1 to 6 carbon atoms, a straight chain or branched monohydroxyalkyl group or polyhydroxyalkyl group with 1 to 6 carbon atoms, a straight or branched alkoxyalkyl group with 2 to 6 carbon atoms, a straight or branched monoaminoalkyl group or polyaminoalkyl group with 2 to 6 carbon atoms, or an unsubstituted aromatic or heteroaromatic ring, or a substituted aromatic or heteroaromatic ring having one or more halogen, a $C_1$- to $C_4$-alkyl group, a nitro group, a sulfonic acid group, a carboxylic acid group or a $C_1$- to $C_4$-alkoxy substituent, or an unsubstituted benzyl group, or a benzyl group substituted with one or more halogen atom, a hydroxy group, a $C_1$- to $C_4$- alkyl group, a nitro group or a $C_1$- to $C_4$-alkyoxy group, or $R_1$ together with $R_2$ and/or $R_1'$ together with $R_2'$ represent a $C_3$-diradical bridge. Hair dye compositions containing these new dye compounds and methods of making them are also disclosed.

12 Claims, No Drawings

BIS-PYRAZOLE AZA COMPOUNDS, PROCESSES FOR MAKING THEM, AND HAIR DYE COMPOSITIONS CONTAINING THESE COMPOUNDS

BACKGROUND OF THE INVENTION

The present invention concerns new bis-pyrazole aza compounds, processes for making them and hair dye compositions containing these compounds.

There is an increasing demand for hair dye compositions that dye hair a copper color and chestnut brown to red shades as well as blond and brown to black colors. These requirements can of course be satisfied by oxidation hair dye preparations based on certain developer substances, such as p-aminophenol derivatives, and coupler substances, for example m-aminophenol or m-phenylenediamine derivatives. Addition of so-called direct-dyeing hair dye compounds is frequently required however to optimize the dye colors produced and to provide a uniform dyeing of the hair from the hair roots to the hair tips.

Addition of red dyes is necessarily required to produce brown shades in hair dye compositions that contain direct-dyeing hair dyes exclusively.

Previously nitro dye compounds have been almost exclusively used to attain this objective. There was a further need however for new direct-dyeing dye compounds that have excellent dye properties in the red range.

SUMMARY OF THE INVENTION

It is an object of the present invention to provide new direct-dyeing hair dye compounds that produce dye colors with excellent properties, especially in the red range.

It is another object of the present invention to provide processes for making the aforesaid new direct-dyeing hair dye compounds.

It is a further object of the present invention to provide new hair dye compositions based on the new direct-dyeing dye compounds.

It was surprisingly found that the new bis-pyrazole aza compounds of the following formula I (which is illustrated in one of its allowed tautomeric forms) are suitable as direct-dyeing dye compounds for the red range and attain the aforesaid objects of the invention in an outstanding manner:

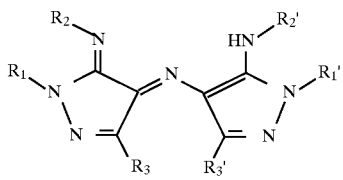

wherein the $R_1$, $R_1'$, $R_2$, $R_2'$, $R_3$ and $R_3'$ groups are the same or different and are each, independently of each other, H, a straight, branched or cyclic alkyl group having 1 to 6 carbon atoms, a straight chain or branched monohydroxyalkyl group or polyhydroxyalkyl group with 1 to 6 carbon atoms, a straight or branched alkoxyalkyl group with 2 to 6 carbon atoms, a straight or branched monoaminoalkyl group or polyaminoalkyl group with 2 to 6 carbon atoms or an aromatic or heteroaromatic ring, which is unsubstituted or has one or more halogen, a $C_1$- to $C_4$-alkyl group, a nitro group, a sulfonic acid group, a carboxylic acid group or a $C_1$- to $C_4$-alkoxy group substituent, or an unsubstituted benzyl group, or a benzyl group substituted with one or more halogen atom, a hydroxy group, a $C_1$- to $C_4$- alkyl group, a nitro group or a $C_1$- to $C_4$-alkyoxy group. Similarly it is possible that $R_1$ together with $R_2$ and/or $R_1'$ together with $R_2'$ represents a $C_3$-diradical bridge.

Preferred compounds according to formula I are those in which $R_1/R_1'$, $R_2/R_2'$ and $R_3/R_3'$ have the following significance, independently of each other: $R_1=R_1'$=a hydrogen, methyl, ethyl, isopropyl, t-butyl, 2-hydroxyethyl, 2,3-dihydroxypropyl, phenyl or benzyl group, wherein the phenyl or benzyl group is unsubstituted or is substituted with one or more halogen atoms, a $C_1$- to $C_4$-alkyl group, a nitro group or a $C_1$- to $C_4$-alkoxy group, and $R_2=R_2'$=a hydrogen, methyl, ethyl, isopropyl, t-butyl, 2-hydroxyethyl, 2,3-dihydroxypropyl, phenyl or benzyl group, wherein the phenyl or benzyl group is unsubstituted or is substituted with one or more halogen atoms, a $C_1$- to $C_4$-alkyl group, a nitro group or a $C_1$- to $C_4$-alkoxy group, and $R_3=R_3'$=a hydrogen, methyl, ethyl, isopropyl, t-butyl, 2-hydroxyethyl, 2,3-dihydroxypropyl, phenyl or benzyl group, wherein the phenyl or benzyl group is unsubstituted or is substituted with one or more halogen atom, a $C_1$- to $C_4$-alkyl group, a nitro group or a $C_1$- to $C_4$-alkoxy group.

Of the above-named preferred compounds of formula I the following are especially preferred: $R_1=R_1'$=methyl, ethyl, isopropyl, t-butyl, 2-hydroxyethyl, 2,3-dihydroxypropyl, phenyl or benzyl, wherein the phenyl or benzyl group is unsubstituted or is substituted with one or more halogen atom, a $C_1$- to $C_4$-alkyl group, a nitro group or a $C_1$- to $C_4$-alkoxy group, and $R_2=R_2'$=a hydrogen, methyl, ethyl, isopropyl, t-butyl, 2-hydroxyethyl, 2,3-dihydroxypropyl or benzyl group, and $R_3=R_3'$=a hydrogen, methyl, ethyl, isopropyl, t-butyl, 2-hydroxyethyl or benzyl group.

The compounds of formula (I) may be present as free bases and as salts of an organic or inorganic acid, especially hydrochloric, nitric, sulfuric, hydrobromic, tartaric, lactic or acetic acid, and particularly as the hydrochloride or sulfate salt.

The following compounds of formula (I) are particularly preferred:

(1) 4-((5-amino-1-methyl-1H-pyrazol-4-yl)imino)-4,5-dihydro-5-imino-1-methyl-1H-pyrazole (II)

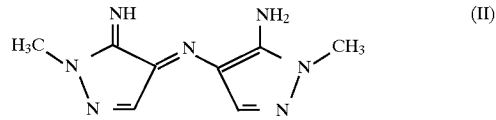

(2) 4-((5-amino-1-isopropyl-1H-pyrazol-4-yl)imino)-4,5-dihydro-5-imino-1-isopropyl-1H-pyrazole (III)

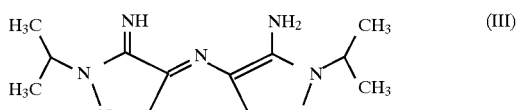

(3) 4-((5-amino-1-(2-hydroxyethyl)-1H-pyrazol-4-yl)imino-4,5-dihydro-1-(2-hydroxyethyl)-5-imino-1H-pyrazole hemisulfate hemihydrate (IV)

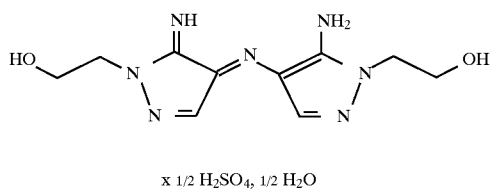

(4) 4-((5-amino-1,3-dimethyl)-1H-pyrazol-4-yl)imino-4,5-dihydro-1,3-dimethyl-5-imino-1H-pyrazole (V):

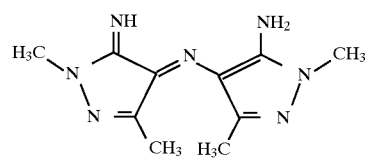

(5) 4-({5-(2-hydroxyethyl)amino-1-methyl-1H-pyrazol-4-yl)imino}-4,5-dihydro-5-(2-hydroxyethyl)imino-1-methyl-1H-pyrazole (VI)

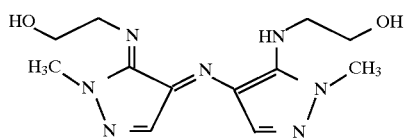

(6) 4-{(5-amino-1-tert.-butyl-3-methyl-1H-pyrazol-4-yl)imino}-4,5-dihydro-1-tert.-butyl-5-imino-3-methyl-1H-pyrazole (VII)

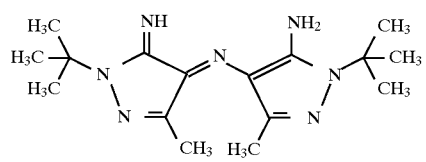

The compounds of formula (II) to (VII) dye hair from a bright orange to a red-violet color shade.

The dye compound according to formula (I) can be made by oxidation of appropriately substituted 1H-pyrazoles ((Ia) and (Ib)). The appropriate pyrazoles are made generally by treatment of 5-aminopyrazoles in the 4-position with nitrous acid and subsequent reduction of the nitro group to the amino group. The pyrazoles used as starting material can be made according to the literature, particularly H. Dorn and H. Dilcher, Liebigs Annalen der Chemie 717, 118(1968) and P. G. Baraldi, et al, Synthesis 1984, 148 and EP-OS 0 375 977 and EP-OS 0 740 931.

The preparation of two-nuclei pyrazoles advantageously occurs by reaction of the pyrazoles of formula (Ia) and (Ib), wherein the groups $R_1$, $R_1'$, $R_2$, $R_2'$, $R_3$ and $R_3'$ have the same significance as previously, according to the following reaction scheme, with an oxidizing agent in a neutral or basic medium, preferably an aqueous, alcoholic or aqueous-alcoholic neutral or basic solution or suspension:

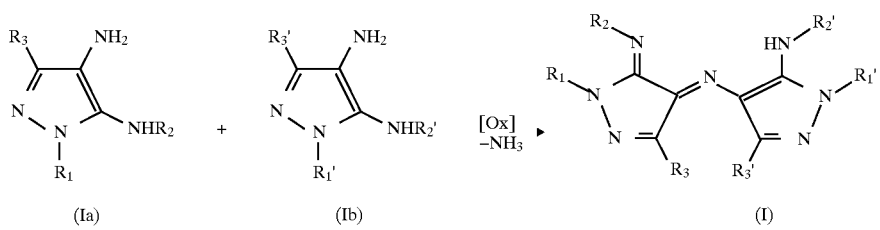

Suitable oxidizing agents include, above all, oxygen, for example in the form of air oxygen or hydrogen peroxide. Other oxidizing agents, can be used in principle, for example potassium hexacyanoferrate, potassium permanganate, potassium dichromate or sodium bromate, but they are only suitable to a limited extent, because, first, many oxidizing agents have their own color and second they form non-volatile residues, which can lead to colored mixed salts during preparation of the product. Ammonia or triethylamine are especially suitable as bases.

The compounds of formula I are basically suitable for dyeing of natural fibers, for example keratin fibers, such as wool and human hair, cotton, jute, sisal linen or silk; modified natural fibers, such as regenerated cellulose, nitrocellulose, alkyl cellulose or hydroxyalkyl cellulose or acetyl cellulose and synthetic fibers, such as polyamide fibers, polyurethane fibers or polyester fibers.

Especially the compounds of formula I are suitable for dyeing hair, particularly human hair.

Compositions for dyeing hair with a content of one or more of the compounds according to the general formula (I) are also the subject of the present invention.

The total content of the bis-pyrazole aza compounds of the formula (I) in the hair dye compositions of the invention amounts to about 0.01 to 4 percent by weight, preferably from 0.02 to 2 percent by weight.

The compositions according to the invention can be used together with an oxidizing agent or without an oxidizing agent. When they are used with an oxidizing agent, a conventional coupler and developer substance are also added.

When the hair dye compositions are used without added oxidizing agents, the compositions according to the invention can also contain additional known direct-dyeing dye compounds from the classes of nitro dye compounds, azo dye compounds, anthraquinone dye compounds and triphenylmethane dye compounds, alone or in mixtures with each other. The added known nitro dye compounds are preferable as the additional known direct-dyeing dye compounds.

Examples of additional nitro dye compounds suitable for use in the composition according to the invention are: 1,4-bis-[(2'-hydroxyethyl)amino]-2-nitrobenzene, 1-(2'-hydroxyethyl)-amino-2-nitro-4-[di(2"-hydroxyethyl)amino]-benzene (HC Blue no. 2),1-amino-3-methyl-4-[(2'-hydroxyethyl)amino]-6-nitro-benzene (HC Violet no. 1),4-[ethyl(2"-hydroxyethyl) -amino-1-[(2"-hydroxyethyl) amino]-2-nitrobenzene hydrochloride (HC Blue no. 12), 4-[di(2'-hydroxyethyl)amino]-1-[(2"-methoxyethyl)amino]-2-nitrobenzene (HC Blue no. 11), 1-[(2',3'-dihydroxypropyl) amino]-4-[methyl-(2'-hydroxyethyl)amino]-2-nitrobenzene hydrochloride (HC Blue no. 10), 1-[(2',3'-dihydroxypropyl) amino]-2-nitro-4-[ethyl-(2"-hydroxyethyl)amino]-2-nitrobenzene hydrochloride (HC Blue no. 9), 1-(3'-hydroxypropylamino)-4-[di(2"-hydroxyethylamino)]-2-nitrobenzene (HC Violet no. 2), 1-methylamino-4-[methyl-(2',3'-dihydroxypropyl)amino]-2-nitrobenzene (HC Blue no. 6), 2-((4-amino-2-nityrophenyl)amino)-5-dimethylaminobenzoic acid (HC Blue no. 13), 1-amino-2-[(2'-hydroxyethyl)amino]-5-nitrobenzene (HC Yellow no. 5), 1-(2'-hydroxyethoxy)-2-[(2"-hydroxyethyl)amino]-5-nitrobenzene (HC Yellow no. 4), 1-[(2'-hydroxyethyl) amino]-2-nitrobenzene (HC Yellow no. 2), 2-[(2'-hydroxyethyl)amino]-1-methoxy- 5-nitrobenzene, 2-amino-3-nitrophenol, 1-(2-hydroxyethoxy)-3-methylamino-4-nitrobenzene, 2,3-(dihydroxypropoxy)-3-methylamino-4-nitrobenzene, 2-[(2'-hydroxyethyl)amino]-5-nitrophenol (HC Yellow no. 11), 3-[(2'-aminoethyl)amino]-1-methoxy-4-nitrobenzene hydrochloride (HC Yellow no. 9), 1-[(2'-ureidoethyl)amino]-4-nitrobenzene, 4-[(2',3'-dihydroxypropyl)amino]-3-nitro-1-trifluormethylbenzene (HC Yellow no. 6),1-chloro-2,4-bis-[(2'-hydroxyethyl) amino]-5-nitrobenzene (HC Yellow no. 10), 4-[(2'-hydroxyethyl)amino]-3-nitro-1-methylbenzene, 1-chloro-4-[(2'-hydroxyethyl)amino]-3-nitrobenzene (HC Yellow no. 12), 4-[(2'-hydroxyethyl)amino]-3-nitro-1-trifluoromethylbenzene (HC Yellow no. 13), 4-[(2'-hydroxyethyl)amino]-3-nitrobenzonitrile (HC Yellow no. 14), 4-[(2'-hydroxyethyl)amino]-3-nitrobenzamide (HC Yellow no. 15), 1-amino-4-[(2'-hydroxyethyl)amino]-2-nitrobenzene (HC Red no. 7), 2-amino-4,6-dinitrophenol, 4-amino-2-nitrodiphenylamine (HC Red no. 1), 1-amino-4-[di(2'-hydroxyethyl)amino]-2-nitrobenzene hydrochloride (HC Red no. 13), 1-amino-5-chloro-4-[(2'-hydroxyethyl) amino]-2-nitrobenzene, 4-amino-1-[(2'-hydroxyethyl) amino]-2-nitrobenzene (HC Red no. 3), 4-amino-3-nitrophenol, 4-[(2'-hydroxyethyl)amino]-3-nitrophenol, 1-[(2'-aminoethyl)amino]-4-(2'-hydroxyethoxy)-2-nitrobenzene (HC Orange no. 2), 4-(2,3-dihydroxypropoxy)-1-[(2-hydroxyethyl)amino]-2-nitrobenzene (HC Orange no. 3), 1-amino-5-chloro-4-[(2',3'-dihydroxypropyl)amino]-2-nitrobenzene (HC Red no. 10), 5-chloro-1,4-[di(2',3'-dihydroxypropyl)amino]- 2-nitrobenzene (HC Red no. 11), 2-[(2'-hydroxyethyl)amino]-4,6-dinitrophenol, 4-ethylamino-3-nitrobenzoic acid, 2-[(4-amino-2-nitrophenyl)amino]-benzoic acid, 2-chloro-6-ethylamino-4-nitrophenol, 2-amino-6-chloro-4-nitrophenol, 4-[(3'-hydroxypropyl)amino]-3-nitrophenol, 2,5-diamino-6-nitropyridine, 1,2,3,4-tetrahydro-6-nitroquinoxaline and 7-amino-3,4-dihydro-6-nitro-2H-1,4-benzoxazine (HC Red 14).

Examples of azo dyes suitable for use in the composition of the invention are: N,N-di(2-hydroxyethyl-3-methyl-4-((4-nitrophenyl)azo)aniline (C.I. 11210), 1-((4-amino-3-nitrophenyl)azo)-7-trimethylammonium)-2-naphthol chloride (Basic Brown 17), 1-(2-hydroxy-4-sulfo-6-nitro) naphthyl-azo-2-naphthol (C.I. 15700), 4-((4-aminophenyl) azo)-1-[di(2-hydroxyethyl)amino]-3-methylbenzene(H.C. Yellow No. 7), 1,4-dimethyl-5-((4-(dimethylamino)phenyl) azo)-1,2,4-triazolium chloride(C.I. 11055), 2-hydroxy-1-((2-methoxyphenyl)azo)-7-(trimethylammonium)-naphthalene chloride (C.I. 12245), 1-(4-aminophenylazo)-2-hydroxy-7-trimethylammonium naphthalene chloride, 4-(3-trimethylammonium-phenylazo)-1-phenyl-3-methylpyrazole-5-one chloride (C.I. 12719), 4-hydroxy-3-[(4-sulfonaphth-1-yl)azo]-naphthalene-1-sulfonic acid disodium salt(C.I. 12720), 1-(4-sulfophenylazo)-2-hydroxynaphthalene(C.I. 15510), 6-hydoxy-5-((4-sulfophenyl)azo)-2-napththalene sulfonic acid disodium salt (C.I. 15985), 4-((4-aminophenyl)azo)-1-[di(2-hydroxyethyl)amino]benzene, 4-((4-aminophenyl)azo)-1-[di(2-hydroxyethyl)amino]-3-methylbenzene (H.C. Yellow 7), 2,6-diamino-3-((pyridin-3-yl)azo)pyridine, 8-amino-1-hydroxy-2-(phenylazo)-3,6-naphthalene disulfonic acid disodium salt (C.I. 17200), 5-acetylamino-4-hydroxy-3-[(2-methylphenyl)azo]-2,7-naphthalene disulfonic acid disodium salt (C.I. 18065) and 4-((2,4-dihydroxy-3-((2,4-dimethylphenyl)azo)phenyl)azo)benzene sulfonic acid sodium salt (C.I. 20170).

Examples of suitable anthraquinone dye compounds are: 1,4-bis-(2,3-dihydroxypropyl)amino-anthraquinone, 1-methylamino-4-(2-hydroxyethyl)amino-anthraquinone, 2-(2-aminoethyl)-amino-anthraquinone, 2-bromo-4,8-diamino-6-(3-trimethylammonium)-phenylamino-1,5-naphthoquinone chloride(C.I. 56059), 1-hydoxy-4-((4-methyl-2-sulfophenyl)amino)-9,10-anthraquinone, 1,4-diaminoanthraquinone, 1-amino-4-cyclohexylamino-2-sulfoanthraquinone, 4-aminopropylamino-1-(methylamino) anthraquinone, 1-aminopropylamino-anthraquinone, 1,4-diamino-2-methoxyanthraquinone and 1,4-dihydroxy-5,8-bis-((2-hydroxyethyl)amino)anthraquinone.

Examples of triphenylmethane dye compounds suitable for use in the composition according to the invention are: 4',4",4"'-triamino-3-methyl-triphenylcarbenium chloride, bis-(4,4-diethylaminophenyl)-4'-ethylamino-naphthylcarbenium chloride, bis-(4,4-dimethylaminophenyl)-4'-phenylamino-naphthylcarbenium chloride (Basic Blue 26, C.I. 44045) and bis-(4-(dimethylamino)phenyl)-(3,7-disulfo-2-hydroxy-naphth-1-yl)carbenium betaine monosodium salt.

The total content of the above-named direct-dyeing nitro dye compounds, azo dye compounds, anthraquinone dye compounds or triphenylmethane dye compounds in the dye compositions according to the invention amounts to from about 0.01 to 4 percent by weight. Preferably the total content of non-oxidation dye compounds in the dye compositions of the invention is from about 0.1 to 5.0 percent by weight.

The form of the hair dye compositions of the invention containing the compounds of formula (I) and direct-dyeing dye compounds, as needed, can, for example, be a solution, especially an aqueous-alcoholic solution. Preferred preparation forms are creams, gels or emulsions. Similarly it is possible to dispense these compositions with the help of an atomizer or other suitable pumping devices or spraying devices or to dispense it in a mixture with conventional condensed propellants under pressure as an aerosol spay or aerosol form from a pressurized container.

The pH of this dye composition is from 3 to 12, especially from 8 to 11.5. The pH of the composition is adjusted to a predetermined alkaline pH value preferably with ammonia, however organic amines, for example monoethanolamine or triethanolamine can also be used. The pH of the composition is adjusted to a predetermined acid pH value with a dilute organic or inorganic acid, such as hydrochloric acid, sulfuric acid, phosphoric acid, ascorbic acid or lactic acid.

The dye composition according to the invention is employed in the conventional manner by applying an amount of the composition sufficient for dyeing to the hair and allowing it to remain in contact with the hair for a sufficiently long time, preferably from 15 to 30 minutes. Subsequently the hair is washed with water, then, if necessary, rinsed with an aqueous solution of a weak organic acid and subsequently dried. The solution of the weak organic acid can be, for example, a dilute aqueous solution of acetic acid, citric acid or tartaric acid.

The above-described hair dye composition without addition of an oxidizing agent can also contain conventional natural or synthetic polymers or modified natural polymers suitable for cosmetic purposes so that hair can be fixed at the same time it is being dyed. This type of composition is designated generally as a tinting-fixing agent or a dyeing-fixing agent.

Synthetic polymers known for this purpose in the cosmetic arts include, for example, polyvinyl pyrrolidone, polyvinyl acetate, polyvinyl alcohol or polyacrylic compounds, such as polyacrylic acid or polymethacrylic acid, basic polymerizates of esters of polyacrylic acid, polymethyl acrylic acid and aminoalcohols or their salts or quaternarized products, polyacrylic nitriles, polyvinyl acetate and copolymerizates of these compounds, such as polyvinyl pyrrolidone-vinyl acetate. The natural or modified natural polymers that can be used include, for example, chitosan (deacetylated chitin) or chitosan derivatives.

The above-named polymers can be contained in the composition according to the invention in the usual amounts suitable for their purposes, especially in an amount of from about 1 to 5 percent by weight. The pH of the tinting-fixing agent or dyeing-fixing agent should be from about 6.0 to 9.0.

The hair dye composition with an additional fixing agent is employed in the known conventional manner by moistening the hair with the fixing agent, setting the hair in a hair-do and subsequently drying.

Understandably the above-described hair dye composition without added oxidizing agent can, if necessary, contain conventional cosmetic additive ingredients for hair dye compositions, for example care-giving substances, wetting agents, thickeners, softeners, preservatives and perfume oils as well as other minor conventional additives included in oxidation hair dye compositions.

As already mentioned, the subject matter of the present invention includes hair dye composition in which addition of an oxidizing agent is required. These dye compositions contain known oxidation dye precursors that are needed for the oxidative treatment (coupler substances and developer substances) besides the dye compounds of the formula (I) and, if necessary, additional conventional direct-dyeing dye compounds directly applicable to the hair selected from the group consisting of nitro dye compounds, azo dye compounds, anthraquinone dye compounds and triphenylmethane dye compounds.

The developer substances that can be used in the compositions according to the invention include aromatic compounds selected from the group consisting of p-phenylenediamine, p-aminophenols and 4,5-diaminopyrazoles, for example 1,4-diaminobenzene(p-phenylenediamine), 1,4-diamino-2-methylbenzene(p-toluylenediamine), 1,4-diamino-2,6-dimethylbenzene, 1,4-diamino-2,5-dimethylbenzene, 1,4-diamino-2,3-diemthylbenzene, 2-chloro-1,4-diaminobenzene, 4-phenylaminoaniline, 4-dimethylaminoaniline, 4-diethylaminoaniline, 4-[di(2-hydroxyethyl)amino]aniline, 4-[(2-methoxyethyl)amino]aniline, 4-[(3-hydroxypropyl) amino]-aniline, 1,4-diamino-2-(2-hydroxyethyl)benzene, 1,4-diamino-2-(1-methylethyl)benzene, 1,3-bis-[(4-aminophenyl)(2-hydroxyethyl)amino]-2-propanol, 1,8-bis-(2,5-diaminophenoxy)-3,6-dioxoctane, 4-aminophenol, 4-amino-3-methylphenol, 4-methylaminophenol, 4-amino-2-(aminomethyl)phenol, 4-amino-2-[(2-hydroxyethyl) amino]methylphenol, 4-amino-2-(methoxymethyl)-phenol, 4-amino-2- (2-hydroxyethyl)phenol, 5-aminosalicylic acid, 2,5-diaminopyridine, 2,4,5,6-tetraaminopyrimidine, 2,5,6-triamino-4-(1H)-pyrimidone, 4,5-diamino-1-(2-hydroxyethyl)-1H-pyrazole, 4,5-diamino-1-(1-methylethyl)-1H-pyrazole, 4,5-diamino-1-[(4-methylphenyl)methyl]-1H-pyrazole, 1-[(4-chlorophenyl)methyl]-4,5-diamino-1H-pyrazole 4,5-diamino-1-methyl-1Hpyrazole, 4,5-diamino-1, 3-dimethylpyrazole, 2,4-diamino-3-tert.-butyl-1-(2-hydroxyethyl)pyrazole, 2,4-diamino-1-methyl-3-phenylpyrazole, 2-aminophenol, 2-amino-6-methylphenol and 2-amino-5-methylphenol. The forgoing developer compounds can be used in the compositions of the invention, either alone or in combinations with each other.

The coupler substances that can be used in the compositions according to the invention include m-phenylenediamines, m-aminophenols or resorcinols, for example 2,4-diamino-1,5-di(2-hydroxyethoxy)benzene, N-(3-dimethylaminophenyl) urea, 2,6-diaminopyridine, 2-amino-4-[(2-hydroxyethyl)amino]anisole, 2,4-diamino-1-fluoro-5-methylbenzene, 2,4-diamino-1-methoxy-5-methylbenzene, 2,4-diamino-1-ethoxy-5-methylbenzene, 2,4-diamino-1-(2-hydroxyethoxy)-5-methylbenzene, 2,4-di[(2-hydroxyethyl)-amino]-1,5-dimethoxybenzene, 2,3-diamino-6-methoxypyridine, 3-amino-6-methoxy-2-(methylamino)pyridine, 1,3-diamino-3,5-dimethoxypyridine, 3,5-diamino-2,6-dimethoxypyridine, 1,3-diaminobenzene, 2,4-diamino-1-(2-hydroxyethoxy) benzene, 2,4-diamino-1,5-di(2-hydroxyethoxy)benzene, 1-(2-aminoethoxy)-2,4-diaminobenzene, 2-amino-1-(2-hydroxyethoxy)benzene, 2,4-diaminophenoxyacetic acid, 3-[di(2-hydroxyethyl)amino]-aniline, 4-amino-2-di[(2-hydroxyethyl)amino]-1-ethoxybenzene, 5-methyl-2-(1-methylethyl)phenol, 3-[(2-hydroxyethyl)amino]aniline, 3-[(2-aminoethyl)-amino]aniline, 1,3-di(2,4-diaminophenoxy) propane, di(2,4-diaminophenoxy)methane, 1,3-diamino-2, 4-dimethoxybenzene, 2,6-bis-(2-hydroxyethyl) aminotoluene, 4-hydroxyindole, 3-dimethylaminophenol, 3-diethylaminophenol, 5-amino-4-fluoro-2-methylphenol, 5-amino-4-methoxy-2-methylphenol, 5-amino-4-ethoxy-2-methylphenol, 3-amino-2,4-dichlorophenol, 5-amino-2,4-dichlorophenol, 3-amino-2-methylphenol, 3-amino-2-chloro-6-methylphenol, 3-aminophenol, 2-[(3-hydroxyphenyl)-amino]acetamide, 5-[(2-hydroxyethyl) amino]-2-methylphenol, 3-[(2-hydroxyethyl)amino]phenol, 3-[(2-methoxyethyl)-amino]phenol, 5-amino-2-ethylphenol, 2-(4-amino-2-hydroxyphenoxy)ethanol, 5-[(3-hydroxypropyl)amino]-2-methylphenol, 3-[(2,3-dihydroxypropyl)amino]-2-methylphenol,3-[(2-hydroxyethyl)amino]-2-methylphenol, 2-amino-3-hydroxypyridine, 5-amino-4-chloro-2-methylphenol, 1-naphthol, 1,5-dihydroxynaphthalene, 1,7-dihydroxynaphthalene, 2,3-dihydroxynaphthalene, 2,7-dihydroxynaphthalene, 2-methyl-1-naphthol acetate, 1,3-dihydroxybenzene, 1-chloro-2,4-dihydroxybenzene, 2-chloro-1,3-dihydroxybenzene, 1,2-dichloro-3,5-dihydroxy-4-methylbenzene, 1,5-dichloro-2,4-dihydroxybenzene, 1,3-dihydroxy-2-methylbenzene, 3,4-methylenedioxyphenol, 3,4-methylenedioxyaniline, 3,4-diaminobenzoic acid, 3,4- dihydro-6-hydroxy-1,4(2H)-benzoxazine, 6-amino-3,4-dihydro-1,4(2H)-benzoxazine, 3-methyl-1-phenyl-5-pyrazolone, 5,6-dihydroxyindole, 5,6-dihydroxyindolene, 5-hydroxyindole, 6-hydroxyindole, 7-hydroxyindole and 2,3-indolendione. The foregoing coupler compounds can be used in the compositions of the invention, either alone or in combinations with each other.

Additional known and conventional oxidation hair dye compounds used for hair dyeing are described in E. Sagrin, "Cosmetics, Science and Technology" (1957), Interscience Publishers Inc., New York, p. 503 ff, and in J. Janistyn, "Handbuch der Kosmetika und Riechstoffe, Band 3(Handbook of Cosmetics and Perfumes, Vol 3)", pp. 388 to 397.

Very good natural blond and brown colors, and also fashionable color shades, may be produced with combinations of the oxidation dye compounds and the compounds of formula (I) above.

The dye compounds according to the invention of formula (I) are contained in the hair dye compositions of the invention with an oxidizing agent addition in an amount of from about 0.01 to 4.0 percent by weight, preferably from 0.02 to 2.0 percent by weight. The total content of non-oxidation dye compounds in these compositions is preferably from about 0.1 to 5.0 percent by weight.

The total concentration of oxidation dye pre-cursors in the oxidation hair dye composition according to the invention amounts to from about 0.1 to 10 percent by weight, preferably from 0.2 to 2 percent by weight.

The oxidation hair dye composition can be acidic, neutral or basic. It can have a pH of 6 to 12, particularly a pH of about 8.0 to 11.5 is preferable. The adjustment of the pH is usually performed with ammonia, but organic amines, for example monoethanolamine or triethanolamine, can also be used.

The oxidizing agent for developing the hair color is usually hydrogen peroxide and/or its addition compounds. The preparation form of the oxidation hair dye composition according to the invention can be the same as the non-oxidation hair dye composition according to the invention and is preferably a cream or a gel.

Conventional cosmetic additive ingredients for the compositions according to the invention in solutions, creams, emulsion or gels include, for example, solvents, such as water, lower aliphatic monohydric or polyhydric alcohols, their esters and ethers, for example alkanols, especially having 1 to 4 carbon atoms, for example, ethanol, propanol or isopropanol, butanol, isobutanol; dihydric and trihydric alcohols, especially those with from 2 to 6 carbon atoms, for example ethylene glycol, propylene glycol, 1,3-propanediol, 1,4-butanediol, 1,5-pentanediol, 1,6-hexanediol, 1,2,6-hexanetriol, glycerol, diethylene glycol, dipropylene glycol; polyalkylene glycols, such as triethylene glycol, polyethylene glycol, tripropylene glycol, polypropylene glycol; lower alkyl ethers of polyhydric alcohols, such as ethylene glycol monomethyl ether, ethylene glycol monoethyl ether, ethylene glycol monopropyl ether or ethylene glycol monobutyl ether, diethylene glycol monomethyl ether or diethylene glycol monoethyl ether, triethylene glycol monomethyl ether or triethylene glycol monoethyl ether; ketones and ketoalcohols, especially those with 3 to 7 carbon atoms, such as acetone, methylethyl ketone, diethyl ketone, methyl isobutyl ketone, methyl phenyl ketone, cyclopentanone, cyclohexanone and diacetone alcohol; ethers, such as dibutyl ether, tetrahydrofuran, dioxan, diisopropyl ether; esters, such as ethyl formate, methyl formate, methyl acetate, ethyl acetate, propylene acetate, butyl acetate, phenyl acetate, ethylene glycol monoethyl ether acetate and acetic acid hydroxyethyl ester; amides, for example dimethyl formamide and dimethyl acetamide, N-methyl pyrrolidone, urea, tetramethyl urea and thioglycol.

Also the hair dye compositions according to the invention can contain wetting agents or emulsifiers from the classes of anionic, cationic, amphoteric, nonionic or zwitter-ionic surfactants, such as fatty alcohol sulfates, alkane sulfonates, alkylbenzene sulfonates, alkyltrimethyl ammonium salts, alkyl betaine, α-olefin sulfonates, ethoxylated fatty alcohols, ethoxylated nonylphenols, fatty acid alkanol amines, ethoxylated fatty acid esters, fatty alcohol polyglycol ether sulfates, alkylpolyglucosides; thickeners, such as higher fatty alcohols, starches, alginates, bentonites, cellulose derivative compounds, petrolatum(Vaseline®), paraffin oil and fatty acids; water-soluble polymeric thickeners, such as natural gums including guar gums, xanthan gums, locust bean meal, pectin, dextran, agar—agar, amylose, amylopectin, dextrin, clays, entirely synthetic hydrocolloids, such as polyvinyl alcohol; care-giving materials, such as lanolin derivative compounds, cholesterol, pantothenic acid, water-soluble cationic polymers, protein derivative compounds, pro-vitamins, vitamins, plant extracts, sugar and betaine; and auxiliary substances, such as moisturizers, electrolytes, antioxidants, fatty amides, sequestering agents, film-forming agents and preservatives.

The above-mentioned ingredients are used in the usual amounts according to their purpose, for example the wetting agents and emulsifiers in concentrations of from about 0.5 to 30 percent by weight, the thickeners in amounts of from about 0.1 to 25 percent by weight and the care-giving materials in amounts of from about 0.1 to 5 percent by weight.

The oxidation hair dye compositions according to the invention are used in the standard manner. The oxidation hair dye composition is mixed with an oxidizing agent prior to treatment and applied to the hair in an amount sufficient for dyeing the hair, usually from about 50 to 150 grams. After an acting time sufficient for the dyeing of the hair, which usually amounts to from about 10 to 45 minutes, the hair is rinsed with water. If necessary it is then washed with a shampoo and/or with an aqueous solution of a weak organic acid, such as citric or tartaric acid, after-rinsed and then dried.

In regard to its dyeing possibilities the hair dye composition according to the invention provides a broad palette of different color shades according to the type and composition of the dye ingredients, which extend from natural color shades to high fashion, bright colors. The dye composition according to the invention is employed either in combination with an oxidizing agent or without addition of an oxidizing agent.

The following examples should illustrate the invention further without limiting the claims appended hereinbelow.

EXAMPLES

Synthesis Examples

Example 1: Synthesis of 4-((5-amino-1-methyl-1H-pyrazol-4-yl)imino)-4,5-dihydro-5-imino-1-methyl-1H-pyrazole (II)

18.5 g of 4,5-diamino-1-methyl-1H-pyrazole dihydrochloride were dissolved in 50 ml water and the pH was adjusted to 9 by addition of concentrated ammonia. Subsequently the resulting solution was reacted with 17 ml of 30% hydrogen peroxide. The solution spontaneously turned a dark red color. The pH was of the solution was adjusted to 12 after 1 hour with concentrated sodium hydroxide and subjected to a vacuum filtration to separate the precipitated dye compound. 7.8 g of dark red crystals with a melting point of over 250° C. (with decomposition) resulted after washing with water and drying in vacuum.

Mass Spectrum: $M^+ =205$ $^1$NMR(DMSO-d$_6$): δ(TMS)=8.24 ppm(s,2H),3.60 ppm(s, 6H)

$\lambda_{max}[H_2O]=478$ nm

Example 2: Synthesis of 4-((5-amino-1-isopropyl-1H-pyrazol-4-yl)imino)-4,5-dihydro-5-imino-1-isopropyl-1H-pyrazole (III)

23.8 grams of 4,5-diamino-1-isopropyl-1H-pyrazole sulfate were suspended in 240 ml isopropanol with 40.5 g of triethylamine and were stirred with a gassing stirrer for 24 hours. After a few minutes a dark red solution is obtained and the product begins to crystallize out of this solution after about 1 hour. The dye compound is filtered off and suspended in a mixture of 300 ml water and 69.6 ml 1N sodium hydroxide for 30 minutes to release the basic dye compound. 8.8 g of dark red crystals with a melting point of 174.4° C. (with decomposition) were obtained after filtration and subsequent washing with some ice water.

$\lambda_{max}[H_2O]=480$ nm

Elemental analysis: $C_{12}H_{19}N_7$ (MW 261.33)

|  | C | H | N |
|---|---|---|---|
| Calculated: | 55.15% | 7.33% | 37.52% |
| Found: | 55.45% | 7.44% | 37.18% |

Example 3: Synthesis of 4-((5-amino-1-(2-hydroxyethyl)-1H-pyrazol-4-yl) imino) -4,5-dihydro-1- (2-hydroxyethyl)-5-imino-1H-pyrazole hemisulfate hemihydrate (IV)

24 g of 4, 5-diamino-1- (2-hydroxyethyl) -1H-pyrazole sulfate were suspended in a mixture of 30 ml water and 20 ml ethanol. The pH of the resulting suspension was adjusted to a pH of 9 with concentrated ammonia and reacted with 17 ml of 30% hydrogen peroxide. The solution turned a dark red color spontaneously. The solution was neutralized with dilute sulfuric acid after one hour and concentrated to half its volume in a rotary evaporator. Then it was stirred into an ice bath. 12 grams of dark red crystals with a metallic surface appearance were produced. Their melting point was 233° C.

$\lambda_{max}[H_2O]=491$ nm

Elemental analysis: $C_{10}H_{15}N_7O_2 \times 0.5\ H_2SO_4 \times 0.5\ H_2O$ (MW=323.33)

|  | C | H | N | S |
|---|---|---|---|---|
| Calculated: | 37.15% | 5.29% | 30.32% | 5.05% |
| Found: | 37.25% | 5.37% | 30.37% | 5.03% |

The structure of this compound was determined by X-ray structure analysis.

Example 4: Synthesis of 4-((5-amino-1,3-dimethyl)-1H-pyrazol-4-yl)imino-4,5-dihydro-1,3-dimethyl-5-imino-1H-pyrazole (V)

19.9 g of 4,5-diamino-1,3-dimethyl-1H-pyrazole dihydrochloride were dissolved in 50 ml water, the pH was adjusted to 9 with concentrated ammonia and the dihydrochloride was reacted with 17 ml of hydrogen peroxide. The resulting solution turned a dark red color spontaneously. After 2 hours the resulting dye compound was separated by filtration and washed with some isopropanol. The crude product was a red dye with $\lambda_{max}[H_2O]=537$ nm and a yellow side product with $\lambda_{max}[H_2O]=419$ nm.

Example 5: 4-((5-(2-hydroxyethyl)amino-1-methyl-1H-pyrazol-4-yl)imino)-4,5-dihydro-5-(2-hydroxyethyl)imino-1-methyl-1H-pyrazole (VI)

22.9 grams of 4-amino-5-(2-hydroxyethyl)amino-1H-pyrazole dihydrochloride were reacted in the same manner as the dihydrochloride of example 4. 3.7 g of a crude product containing impurities were obtained.

$^1$H-NMR(DMSO-d$_6$): δ(TMS)=8.50 ppm(s,broad,3H), 8.16 ppm(s,2H), 3.60 ppm(m,14H)

$\lambda_{max}[H_2O]=488$ nm

Example 6: 4-((5-amino-3-methyl-1-phenyl-1H-pyrazole-4-yl)imino)-4,5-dihydro-5-imino-3-methyl-1H-pyrazole (VII)

2.6 g 4,5-diamino-3-methyl-1-phenyl-1H-pyrazole dihydrochloride were dissolved in a mixture of 30 ml water and 30 ml ethanol. The pH of the resulting solution was then adjusted to 9 with concentrated ammonia. Subsequently the reaction mixture was stirred for 17 hours with a gasifying stirrer. The precipitated dye compounds was separated by filtration, washed with water and dried. The yield amounted to 1.2 g.

Melting point: >250° C.

Elemental analysis: $C_{20}H_{19}N_7$ (MW=357.42)

|  | C | H | N |
|---|---|---|---|
| Calculated: | 67.21% | 5.36% | 27.43% |
| Found: | 67.13% | 5.36% | 27.33% |

Examples of Hair Dye Compositions

Examples 7 to 12: Hair Dye Solutions, basic

The following dye solutions were prepared:

10.0 g isopropanol 10.0 g lauryl alcohol diglycol ether sulfate sodium salt (28% aqueous solution)

10.0 g ammonia (27% aqueous solution)

0.3 g ascorbic acid

X g Dye Precursor compounds and dye compounds From Table 1 ad 100.0 g water, salt-free

Prior to application 10 g of each hair dye solution were mixed with 10 g of hydrogen peroxide solution (6 aqueous solution). The ready-to-use hair dyeing mixture was applied to the hair. After an acting time of 20 minutes at 40° C., the hair was rinsed with water, shampooed and dried. The color of the dyed hair resulting from use of these solutions and their composition are summarized in the following Table I.

TABLE I

HAIR COLOR PRODUCED BY HAIR DYE COMPOSITIONS ACCORDING TO THE INVENTION

| | Amount in grams | | | | | |
|---|---|---|---|---|---|---|
| Example: | 7 | 8 | 9 | 10 | 11 | 12 |
| Dye Precursor Or Dye Compound | | | | | | |
| 4-amino-2-aminomethyl-phenol dihydrochloride | 0.7 | 0.6 | — | 0.4 | — | 0.1 |

TABLE I-continued

HAIR COLOR PRODUCED BY HAIR DYE COMPOSITIONS ACCORDING TO THE INVENTION

| Example: | 7 | 8 | 9 | 10 | 11 | 12 |
|---|---|---|---|---|---|---|
| | | | Amount in grams | | | |
| 2,5-diaminotoluene sulfate | — | — | — | 0.1 | — | — |
| 2-(2,5-diaminophenyl)-ethanol sulfate | — | 0.1 | — | — | — | — |
| 4-amino-3-methyphenol | — | — | 0.2 | — | — | — |
| 4-(di(2-hydroxyethyl)-amino) aniline | — | — | — | — | — | 0.2 |
| 4,5-diamino-1-hydroxyethyl pyrazole sulfate | — | — | — | 0.1 | — | 0.1 |
| tetraaminopyrimidine sulfate hydrate | — | — | — | — | 0.2 | — |
| resorcinol | 0.4 | — | — | — | — | — |
| 3-aminophenol | — | 0.4 | — | — | — | 0.2 |
| 5-amino-2-methylphenol | — | — | — | — | — | 0.1 |
| 2-amino-4-((2-hydroxyethyl) amino) anisole sulfate | — | — | — | — | 0.4 | — |
| 2,4-diamino-1-(2-hydroxyethoxy) benzene dihydrochloride | — | — | 0.1 | — | — | — |
| N-(3-(dimethylamino)-Phenyl) urea | — | — | — | 0.5 | — | — |
| Dye Compound(III) (example 2) | 0.4 | — | — | 0.2 | — | — |
| Dye compound (IV) (example 3) | — | 0.3 | 0.3 | — | — | — |
| Dye Compound (VI) (example 5) | — | — | — | — | 0.4 | 0.4 |
| Color Obtained | copper-Blond | bright chestnut | brick red | dark auburn | baccara | ruby-red |

Example 13: Hair Dye Composition in the form of a Cream 0.40 g 2,5-diaminotoluene sulfate 0.60 g 4-amino-2-aminomethylphenol dihydrochloride 0.30 g resorcinol 0.10 g m-aminophenol 0.05 g 4-hydroxyindole 0.10 g 5-amino-2-methylphenol 0.10 g 2-amino-6-chloro-4-nitrophenol 15.00 g cetyl alcohol 3.50 g sodium lauryl alcohol diglycol ether sulfate, (28% aqueous solution)

3.00 g ammonia, 25% aqueous solution 0.30 g sodium sulfite, water-free 0.10 g Dye Compound (V)(according to example 4) to 100.00 g water, demineralized 50 g of this hair dye composition were mixed with 50 g of hydrogen peroxide solution (6% aqueous solution) shortly prior to use. Subsequently the mixture was applied to blond natural hair and allowed to act on it for 30 minutes at 40° C. After that the hair was rinsed with water and dried. The hair had a chestnut-brown color with a reddish copper reflection.

Example 14: Hair Dye Composition in the form of a Cream 0.30 g 2,5-diaminotoluene sulfate 0.20 g 2-(2,5-diaminophenyl)ethanol sulfate 0.04 g 4-amino-3-methylphenol 0.10 g 4-amino-2-aminomethylphenol dihydrochloride 0.20 g resorcinol 0.20 g 2-methylresorcinol 0.03 g 3-aminophenol 0.07 g 5-amino-2-methylphenol 0.02 g 5-((2-hydroxyethyl)amino)-2-methylphenol hemisulfate 0.10 g 2,4-diamino-1-fluoro-5-methylbenzene sulfate hydrate 0.10 g 2,4-diamino-1,5-di(2-hydroxyethoxy)benzene 0.15 g dye compound (IV)(according to example 3)

15.00 g cetyl alcohol 3.50 g sodium lauryl alcohol diglycol ether sulfate, (28% aqueous solution)

3.00 g ammonia, 25% aqueous solution 0.30 g sodium sulfite, water-free 0.20 g ascorbic acid to 100.00 g water, demineralized 50 g of this hair dye composition were mixed with 50 g of hydrogen peroxide solution (6% aqueous solution) shortly prior to use. Subsequently the mixture was applied to blond natural hair and allowed to act on it for 20 minutes at 40° C. After that the hair was rinsed with water and dried. The hair had an anthracite basic color with an auburn reflection.

Example 15: Hair Dye composition in Gel form 0.50 g 2,5-diaminotoluene sulfate 0.30 g 3-dimethylaminophenylurea 0.10 g 1-naphthol 0.40 g sodium hydroxide 0.50 g ascorbic acid 7.00 g isopropyl alcohol 3.00 g glycerol 15.00 g oleic acid 10.00 g ammonia, (25% aqueous solution)

0.10 g Dye Compound (III)(according to example 2) to 100.00 g water, demineralized 50 g of this hair dye composition were mixed with 50 g of hydrogen peroxide solution (6% aqueous solution) shortly prior to use. Subsequently the mixture was applied to blond human hair and allowed to act on it for 30 minutes. After that the hair was rinsed with water and dried. The hair had an intense auburn shade.

Example 16: Hair Dye Solution, acidic 0.60 g 4-amino-2-aminomethylphenol dihydrochloride 0.10 g resorcinol 0.30 g 4-chlororesorcinol 0.30 g ascorbic acid 0.30 g sodium lauryl ether sulfate 1.10 g ammonia, (25% aqueous solution)

0.10 g Dye Compound (II)(according to example 1) to 100.00 g water, demineralized The pH of the dye carrier is adjusted with a dilute ammonia solution or dilute hydrochloric acid solution to a pH value of 6.8. Immediately prior to use 20 grams of the hair dye solution are mixed with 20 g of 6 percent aqueous solution of hydrogen peroxide (pH=6.8) and the obtained ready-to-use oxidation hair dye mixture (pH=6.8) is applied to bleached hair. After an acting time of 30 minutes at room temperature the hair is rinsed with water and dried. The hair treated in this manner had a bright copper color.

Example 17: Hair Dye Solution, non-oxidative 0.05 g Basic Blue 7 (C.I. 42595)

0.03 g 1-methylamino-4-[N-methyl-N-(2,3-dihydroxypropyl)amino]-2-nitrobenzene 0.15 g N-(2,3-dihydroxypropyl)-2-nitro-4-trifluoromethyl-aniline 0.15 g Dye Compound (IV)(according to example 3) to 100.00 g water, demineralized The pH of the dye carrier is adjusted with a dilute ammonia solution or dilute hydrochloric acid solution to a pH value of 6.8. The resulting dye solution (pH=6.8) is applied to bleached hair. After an acting time of 20 minutes at 40° C. the hair is rinsed with water and dried. The hair treated in this manner had a chestnut brown color.

Examples 18 to 20: Hair Dye Compositions, non-oxidative

The following solutions were prepared:

10.0 g isopropanol 1.0 g hydroxyethyl cellulose

X g dye compound according to Table II

To 100.0 g water, demineralized

The pH value given in Table II is obtained by citric acid or sodium hydroxide addition. The colors obtained and the compositions of the solutions are summarized in Table II.

TABLE II

HAIR COLOR PRODUCED BY HAIR DYE COMPOSITIONS ACCORDING TO THE INVENTION

| | Amount in grams | | |
|---|---|---|---|
| Example: | 18 | 19 | 20 |
| Dye Precursor or Dye Compound | | | |
| 1-(2-hydroxyethyl)amino-4-[di(2-hydoxyethyl)-amino]-2-nitrobenzene | 0.4 | — | — |
| 4-[ethyl-(2-hydroxyethyl)-amino]-1-[(2-hydroxyethyl)-amino]-2-nitrobenzene hydrochloride | — | 0.8 | 0.2 |
| 1-amino-5-chloro-4-[(2,3-dihydroxypropyl)-amino]-2-nitrobenzene | 0.1 | 0.03 | — |
| 2-amino-6-chloro-4-nitrophenol hydrochloride | — | 0.2 | 0.2 |
| 4-[(2-hydroxyethyl)amino]-3-nitrotoluene | 0.4 | 0.2 | — |
| 4-[(2,3-dihydroxypropyl)-amino]-3-nitro-1-trifluoro-methylbenzene | — | 0.1 | 0.5 |
| Basic Blue 7 | — | 0.03 | 0.05 |
| Dye Compound (II) (example 1) | 0.05 | 0.1 | — |
| Dye Compound (VI) (example 5) | — | 0.05 | 0.1 |
| pH | 6.8 | 7.5 | 8.0 |
| Color Obtained | chestnut | mahogany | copper |

Examples 21: Hair Dye Composition with Fixing Action 2.00 g polyvinyl pyrrolidone 0.10 g glycerol 40.00 g ethanol 0.15 g N-(2,3-dihydroxypropyl)-2-nitrotrifluoromethyl aniline X g dye compound (III)(according to example 2)

To 100.0 g water, demineralized

White human hair was moistened with the above-described dyeing and fixing solution, set in a hair-do and dried. The hair so treated had a reddish gleam and was fixed.

The disclosure of German Patent Application 197 30 412.5 of Jul. 16, 1997 is hereby explicitly incorporated by reference. This German Patent Application discloses the same invention as described herein and claimed in the claims appended hereinbelow and is the basis for a claim of priority for the instant invention under 35 U.S.C. 119.

While the invention has been illustrated and described as embodied in bis-pyrazole aza compounds, processes for making them, and hair dye compositions containing these compounds, it is not intended to be limited to the details shown, since various modifications and changes may be made without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed is new and is set forth in the following appended claims:

1. A bis-pyrazole aza compound of formula (I):

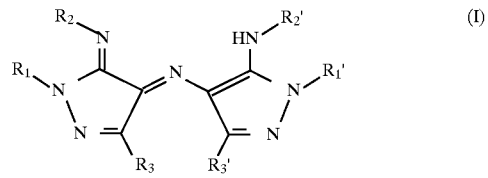

wherein $R_1$, $R_1'$, $R_2$, $R_2'$, $R_3$ and $R_3'$ are each, independently of each other, H, a straight, branched or cyclic alkyl group having 1 to 6 carbon atoms, a straight chain or branched monohydroxy-alkyl group or polyhydroxyalkyl group with 1 to 6 carbon atoms, a straight or branched alkoxyalkyl group with 2 to 6 carbon atoms, a straight or branched monoaminoalkyl group or polyaminoalkyl group with 2 to 6 carbon atoms, or an unsubstituted aromatic or heteroaromatic ring, or a substituted aromatic or heteroaromatic ring having one or more halogen, a $C_1$- to $C_4$-alkyl group, a nitro group, a sulfonic acid group, a carboxylic acid group or a $C_1$- to $C_4$-alkoxy group substituent, or an unsubstituted benzyl group, or a benzyl group substituted with one or more halogen atoms, a hydroxy group, a $C_1$- to $C_4$-alkyl group, a nitro group or a $C_1$- to $C_4$-alkoxy group, or $R_1$ together with $R_2$ and/or $R_1'$ together with $R_2'$ represent a $C_3$-diradical bridge or a salt of an organic or inorganic acid thereof.

2. The bis-pyrazole aza compound as defined in claim 1, wherein $R_1$=$R_1'$=a hydrogen, methyl, ethyl, isopropyl, t-butyl, 2-hydroxyethyl, 2,3-dihydroxypropyl, phenyl or benzyl group, wherein the phenyl or benzyl group is unsubstituted or is substituted with one or more halogen atoms, a $C_1$- to $C_4$-alkyl group, a nitro group or a $C_1$- to $C_4$-alkoxy group, and $R_2$=$R_2'$=hydrogen, methyl, ethyl, isopropyl, t-butyl, 2-hydroxyethyl, 2,3-dihydroxypropyl, phenyl or benzyl group, wherein the phenyl or benzyl group is unsubstituted or is substituted with one or more halogen atoms, a $C_1$- to $C_4$-alkyl group, a nitro group or a $C_1$- to $C_4$-alkoxy group, and $R_3$=$R_3'$=hydrogen, methyl, ethyl, isopropyl, t-butyl, 2-hydroxyethyl, 2,3-dihydroxypropyl, phenyl or benzyl group, wherein the phenyl or benzyl group is unsubstituted or is substituted with one or more halogen atoms, a $C_1$- to $C_4$-alkyl group, a nitro group or a $C_1$- to $C_4$-alkoxy group.

3. The bis-pyrazole aza compound as defined in claim 1, wherein $R_1$=$R_1'$=a methyl, ethyl, isopropyl, t-butyl, 2-hydroxyethyl, 2,3-dihydroxypropyl, phenyl or benzyl group, wherein the phenyl or benzyl group is unsubstituted or is substituted with one or more halogen atoms, a $C_1$- to $C_4$-alkyl group, a nitro group or a $C_1$- to $C_4$-alkoxy group, and $R_2 = R_2' =$ a hydrogen, methyl, ethyl, isopropyl, t-butyl, 2-hydroxyethyl, 2,3-dihydroxypropyl or benzyl group, and $R_3 = R_3' =$ a hydrogen, methyl, ethyl, isopropyl, t-butyl, 2-hydroxyethyl or benzyl group.

4. The bis-pyrazole aza compound as defined in claim 1, selected from the group consisting of 4-((5-amino-1-methyl-1H-pyrazol-4-yl)imino)-4,5-dihydro-5-imino-1-methyl-1H-pyrazole, 4-((5-amino-1-isopropyl-1H-pyrazol-4-yl)imino)- 4,5-dihydro-5-imino-1-isopropyl-1H-pyrazole, 4-((5-amino-1-(2 -hydroxyethyl)-1H-pyrazol-4-yl)imino-4,5-dihydro-1-(2-hydroxyethyl)-5-imino-1H-pyrazole hemisulfate hemihydrate, 4-((5-amino-1,3-dimethyl)-1H-pyrazol-4-yl)imino-4,5-dihydro-1,3-dimethyl-5-imino-1H-pyrazole, 4-[{5-(2-hydroxyethyl)amino-1-methyl-1H-pyrazol-4-yl}imino]-4,5-dihydro-5-(2-hydroxyethyl)imino-1-methyl-1H-pyrazole and 4-{(5-amino-1-tert.-butyl-3-methyl-1H-pyrazol-4-yl)imino}-4,5-dihydro-1-tert.-butyl-5-imino-3-methyl-1H-pyrazole.

5. A composition for dyeing hair containing at least one bis-pyrazole aza compound of the following formula (I):

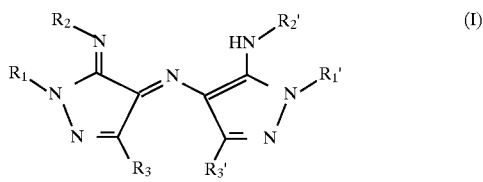

wherein $R_1$, $R_1'$, $R_2$, $R_2'$, $R_3$ and $R_3'$ are each, independently of each other, H, a straight, branched or cyclic alkyl group having 1 to 6 carbon atoms, a straight chain or branched monohydroxy-alkyl group or polyhydroxyalkyl group with 1 to 6 carbon atoms, a straight or branched alkoxyalkyl group with 2 to 6 carbon atoms, a straight or branched monoaminoalkyl group or polyaminoalkyl group with 2 to 6 carbon atoms, or an unsubstituted aromatic or heteroaromatic ring, or a substituted aromatic or heteroaromatic ring having one or more halogen, a $C_1$- to $C_4$-alkyl group, a nitro group, a sulfonic acid group, a carboxylic acid group or a $C_1$- to $C_4$-alkoxy group substituent, or an unsubstituted benzyl group, or a benzyl group substituted with one or more halogen atoms, a hydroxy group, a $C_1$- to $C_4$-alkyl group, a nitro group or a $C_1$- to $C_4$-alkoxy group, or $R_1$ together with $R_2$ and/or $R_1'$ together with $R_2'$ represent a $C_3$- diradical bridge or a salt of an organic or inorganic acid thereof.

6. The composition for dyeing hair as defined in claim 5, further comprising at least one coupler substance and at least one developer substance for oxidative hair dyeing.

7. The composition as defined in claim 6, wherein the at least one developer substance is an aromatic compound selected from the group consisting of p-phenylenediamines, p-aminophenols and 4,5-diaminopyrazoles and the at least one coupler substance is selected from the group consisting of m-phenylenediamines, m-aminophenols and resorcinols.

8. The composition as defined in claim 5, further comprising at least one direct-dyeing dye compound selected from the group consisting of nitro dye compounds, azo dye compounds, anthraquinone dye compounds and triphenylmethane dye compounds.

9. The composition as defined in claim 5, containing from 0.01 to 4 percent by weight of the bis-pyrazole aza compound of the formula (I).

10. The composition as defined in claim 5, further comprising at least one natural polymer, modified-natural polymer and/or synthetic polymer.

11. A process for making the bis-pyrazole aza compound of formula (I), said process comprising reacting a pyrazole of formula (Ia) and a pyrazole of formula (Ib):

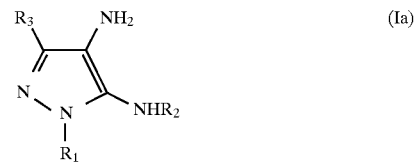

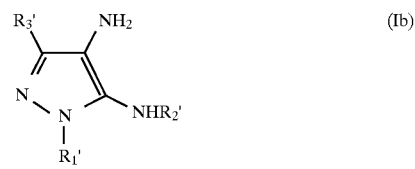

with an oxidizing agent in neutral or basic media;

wherein $R_1$, $R_1'$, $R_2$, $R_2'$, $R_3$ and $R_3'$ groups are each, independently of each other, H, a straight, branched or cyclic alkyl group having 1 to 6 carbon atoms, a straight chain or branched monohydroxyalkyl group or polyhydroxyalkyl group with 1 to 6 carbon atoms, a straight or branched alkoxyalkyl group with 2 to 6 carbon atoms, a straight or branched monoaminoalkyl group or polyaminoalkyl group with 2 to 6 carbon atoms, or an unsubstituted aromatic or heteroaromatic ring, or a substituted aromatic or heteroaromatic ring having one or more halogen, a $C_1$- to $C_4$-alkyl group, a nitro group, a sulfonic acid group, a carboxylic acid group or a $C_1$- to $C_4$-alkoxy group substituent, or an unsubstituted benzyl group, or a benzyl group substituted with one or more halogen atoms, a hydroxy group, a $C_1$- to $C_4$-alkyl group, a nitro group or a $C_1$- to $C_4$-alkoxy group, or $R_1$ together with $R_2$ and/or $R_1'$ together with $R_2'$ represent a $C_3$-diradical bridge or a salt of an organic or inorganic acid thereof.

12. The process as defined in claim 11, wherein the oxidizing agent is hydrogen peroxide or air oxygen.

* * * * *